(12) United States Patent
Feingold et al.

(10) Patent No.: US 7,727,968 B2
(45) Date of Patent: Jun. 1, 2010

(54) COMBINATION THERAPY FOR THE TREATMENT OF ACUTE LEUKEMIA AND MYELODYSPLASTIC SYNDROME

(75) Inventors: Jay Marshall Feingold, Wynnewood, PA (US); Matthew L. Sherman, Newton, MA (US); Lance H. Leopold, Dresher, PA (US); Mark Berger, Merion Station, PA (US)

(73) Assignee: Wyeth LLC, Madison, NJ (US)

( * ) Notice: Subject to any disclaimer, the term of this patent is extended or adjusted under 35 U.S.C. 154(b) by 214 days.

(21) Appl. No.: 11/811,626

(22) Filed: Jun. 11, 2007

(65) Prior Publication Data

US 2007/0269430 A1 Nov. 22, 2007

Related U.S. Application Data

(63) Continuation of application No. 10/700,650, filed on Nov. 4, 2003, now abandoned.

(60) Provisional application No. 60/424,156, filed on Nov. 6, 2002.

(51) Int. Cl.
*A61K 31/70* (2006.01)
(52) U.S. Cl. .................. 514/34; 424/181.1; 514/45; 514/49
(58) Field of Classification Search ............. None
See application file for complete search history.

(56) References Cited

U.S. PATENT DOCUMENTS 5,744,460 A 4/1998 Müller et al.
5,773,001 A * 6/1998 Hamann et al. .......... 424/181.1
2002/0103141 A1 8/2002 McKearn et al.

OTHER PUBLICATIONS

Lowenberg et al (New Journal of Medicine, vol. 341, pp. 1051-1062, 1999.*
Kell et al (Blood (2201) 98-123a-124), 2001.*
R. Berkow et al, The Merck Manual, Sixteenth Edition, pp. 1243-1244. Merck Research Laboratories, Rahway, NJ.(1992).
Mark H. Beers and Robert Berkow, The Merck Manual, Seventeenth Edition, Sec. 11, Ch. 138, pp. 945-955, (1999).
G. Garcia-Manero, et al, Myelodyplastic Syndromes Acute Myeloid Leukemia, Haematologica, vol. 87(8): 804-807 Aug. 2002.
Elihu H. Estey, et al., Gemtuzumab Ozogamicin With or Without Interleukin 11 in Patients 65 Years of Age or Older With Untreated Acute Myeloid Leukemia and High-Risk Myelodysplastic Syndrome: Comparison With Idarubicin Plus Continuous-Infusion, High-Dose Cytosine Arabinoside, Blood, vol. 99(12), pp. 4343-4349, Jun. 2002.

* cited by examiner

*Primary Examiner*—Elli Peselev

(57) ABSTRACT

Methods of treatment and pharmaceutical combinations are provided for the treatment of acute leukemia, such as acute myelogenous leukemia, and myelodysplastic syndrome. The methods of treatment and pharmaceutical combinations employ an anti-CD33 cytotoxic conjugate in combination with at least one compound selected from the group consisting of an anthracycline and a pyrimidine or purine nucleoside analog. Preferred methods of treatment and pharmaceutical combinations employ gemtuzumab ozogamicin, daunorubicin, and cytarabine.

20 Claims, No Drawings

COMBINATION THERAPY FOR THE TREATMENT OF ACUTE LEUKEMIA AND MYELODYSPLASTIC SYNDROME

CROSS REFERENCE TO RELATED APPLICATIONS

This application is a continuation of U.S. application Ser. No. 10/700,650 filed on Nov. 4, 2003, now abandoned which claims the benefit under 35 U.S.C. §119(e) of U.S. provisional application No. 60/424,156 filed on Nov. 6, 2002, the entire disclosures of which are hereby incorporated by reference.

FIELD OF THE INVENTION

Methods of treatment and pharmaceutical combinations are provided for the treatment of acute leukemia, in particular, acute myelogenous leukemia and myelodysplastic syndrome. The methods of treatment and pharmaceutical combinations employ an anti-CD33 cytotoxic conjugate in combination with at least one compound selected from the group consisting of an anthracycline and a pyrimidine or purine nucleoside analog, in particular, gemtuzumab ozogamicin, daunorubicin, and cytarabine.

BACKGROUND OF THE INVENTION

Acute leukemia is typically a rapidly progressing leukemia characterized by replacement of normal bone marrow by blast cells of a clone arising from malignant transformation of a hematopoietic stem cell. There are two types of acute leukemias, acute lymphoblastic leukemia (ALL) and acute myelogenous leukemia (AML). ALL is the most common malignancy in children, but also occurs in adolescents and has a second, lower peak in adults. AML, also know as acute myeloid leukemia and acute myelocytic leukemia, is the more common acute leukemia in adults and its incidence increases with age, but AML also occurs in children. For both types of acute leukemias, the primary goal of treatment is to achieve complete remission, with resolution of abnormal clinical features, return to normal blood counts and normal hematopoiesis in the bone marrow with <5% blast cells, a neutrophil count of >1,000-1,500, a platelet count of >100,000, and disappearance of the leukemic clone; however, the drug regimens for treating ALL and AML have differed. *The Merck Manual*, Sec. 11, Ch. 138 (17$^{th}$ ed. 1999); Estey, E., Cancer (2001) 92(5): 1059-1073. Initial therapy aims at inducing remission. Treatment of AML differs most from ALL in that patients with AML respond to fewer drugs and have a high rate of relapse.

Patients with AML who achieve a complete remission live longer than patients who do not, and only patients who achieve complete remission are potentially cured if their complete remission remains for at least three years. Estey, E., Cancer (2001) 92(5): 1059, 1060. Remission induction rates in patients with AML range from 50 to 85%, with patients older than 50 years, and especially those older than 65 years, less likely to achieve remission. Long-term disease-free survival occurs in a low percentage of patients, 20-40%, and increases to 40-50% in younger patients treated with bone marrow transplants. Patients with secondary AML have a poor prognosis. *The Merck Manual*, Sec. 11, Ch. 138 (17$^{th}$ ed. 1999).

Treatment of AML is problematic because normal stem-cell precursors are sensitive to the agents used, and therapy aimed at myeloid leukemic clones results in destruction of part of the normal stem-cell pool. Induction of remission is usually possible with intensive chemotherapy. Complete remission has been stated to be achievable in up to 80% of younger patients and about 50% of older patients (who form the majority of those with AML), but patients suffer severe neutropenia during induction and remission rate is to some extent dependent upon the standard of supportive care. Remission rates are lower in those with adverse prognostic factors such as poor performance status, AML secondary to myelodysplasia or antineoplastics, high white cell count, features of multidrug resistance, and unfavorable cytogenetics. Löwenberg, B., et al., N. Engl. J. Med. (1999) 341:1051-62; Correction. ibid.; 1484. The greatest unmet medical need is in AML patients over 70 years of age. For these elderly AML patients, complete remission may be difficult to obtain, but an increased benefit in their quality of life is a treatment goal to be achieved.

Established regimens are based on cytarabine, a pyrimidine nucleoside analog, with the anthracycline daunorubicin. Löwenberg, B., et al., N. Engl. J. Med. (1999) 341:1051-62; Correction. ibid.; 1484; Burnett, A. K. & Eden O. B., Lancet (1997) 349:270-275; Hiddemann, W., et al., J. Clin. Oncol. (1999) 17:3569-76. The first successful regimens also included thioguanine, which is still used by some medical centers, although the majority opinion is that it gives no additional advantage and thioguanine has been dropped from most induction protocols. Alternatives to daunorubicin include idarubicin and mitoxantrone. Löwenberg, B., et al., N. Engl. J. Med. (1999) 341:1051-62; Correction. ibid.; 1484. Etoposide has been added to induction protocols of cytarabine and daunorubicin with improved results in younger patients.

The basic induction regimen for treatment of AML includes administration of cytarabine by continuous intravenous (IV) infusion for 7 days, with an anthracycline such as daunorubicin or idarubicin given IV for 3 days during this time, usually in the first three days. *The Merck Manual*, Sec. 11, Ch. 138 (17$^{th}$ ed. 1999). This widely used regimen for the treatment of AML is known as a 3+7 regimen and produces complete remission rates of 60-80%. De Nully Brown, P., et al., Leukemia (1997) 11:37-41. Treatment usually results in significant myelosuppression, often for long periods before marrow recovery. Other adverse events from these two drugs include chemical arachnoiditis, myocardial toxicity, and neurotoxicity. The induction regimen may be repeated, usually up to a total of three times, to achieve remission. Before repeating the induction regimen, a bone marrow analysis is done on after fourteen days from the completion of the last induction regimen. If the bone marrow has been cleaned out, i.e., there is a complete response, then the physician will wait until the patient's peripheral blood counts recover before administering another induction regimen. If the bone marrow analysis shows that disease is still present, i.e., there is a partial or minimal response, then the induction regimen will be repeated without waiting for the patient's peripheral blood counts to recover. The waiting period between induction regimens is therefore twenty-eight to thirty-five days for a complete responder, and fourteen to twenty-one days for partial and minimal responders. For patients with relapsed AML, the standard induction therapy of cytarabine and daunorubicin does not produce a good response rate, typically <40%, and the prognosis is poor for these patients.

After remission is achieved, a second treatment regimen using the same drugs or other drugs to knock out the disease, known as consolidation therapy, may be employed. However, a high percentage of patients suffer from relapse, even in series with intensive post-remission consolidation chemotherapy. De Nully Brown, P., et al., Leukemia (1997) 11:37-41.

The current trend is towards the use of more intensive induction regimens. Use of high-dose cytarabine in doses of up to 3 g/m$^2$ every twelve hours for up to six days per day (with daunorubicin and etoposide) has been reported to improve the duration of first remission and disease-free survival compared with standard doses of cytarabine. Bishop, J. F., et al., Blood (1996) 87:1710-1717. Equally the timing of induction cycles may be important: intensive timing (where the second cycle was given 10 days after the first) has improved disease-free survival, despite more toxicity-related deaths, compared with the standard interval of 14 days or more. Woods, W. G., et al., Blood (1996) 87:4979-4989.

Once remission is induced, further treatment (post remission therapy) is essential in preventing relapse. Löwenberg, B., et al., N. Engl. J. Med. (1999) 341:1051-62; Correction. ibid.; 1484; Burnett, A. K. & Eden O. B., Lancet (1997) 349:270-275; Hiddemann, W., et al., J. Clin. Oncol. (1999) 17:3569-76. Options include further chemotherapy, or allogeneic or autologous bone marrow transplantation. Long-term survival of about 50% may be possible with these options when used in patients in first remission. However, which option to use is controversial. The most successful chemotherapy regimens use high-dose cytarabine for up to 4 courses, and appear to be comparable to bone marrow transplantation in terms of survival. Mayer, R. J. et al., N. Engl. J. Med. (1994) 331:896-903; Cassileth, P. A., et al., N. Engl. J. Med. (1998) 339:1649-1656. Consequently, some advocate a policy of intensive post remission chemotherapy, reserving transplantation for subsequent relapse, particularly for patients with favorable cytogenetics. Edenfield, W. J. & Gore, S. D., Semin. Oncol. (1999) 26:21-34.

Another drug used in the treatment of AML is gemtuzumab ozogamicin (Mylotarg®). Gemtuzumab ozogamicin was approved in May 2000 in the United States of America for the treatment of AML in patients in first relapse who are 60 years old or older and not considered candidates for other cytotoxic chemotherapy. Gemtuzumab ozogamicin is administered as a two-hour IV infusion in a dose of 9 mg/m$^2$. A second dose may be administered fourteen days later. While many patients receiving gemtuzumab ozogamicin have achieved complete remission, a significant number of patients have had a delay in platelet recovery or incomplete platelet recovery. *Physician's Desk Reference* (56$^{th}$ ed. 2002). Hepatic venoocclusive disease (VOD), which is potentially fatal, has occurred in patients who have undergone stem cell transplantation after gemtuzumab ozogamicin therapy. Tack, D. K. et al., Bone Marrow Transplantation (2001) 28(9):895-897. It was also reported in July 2001 that patients receiving gemtuzumab ozogamicin who did not undergo stem cell transplantation developed as much as a 10% increased risk of developing significant hepatotoxicity and possible morbidity and mortality, although most of these patients received gemtuzumab ozogamicin in previously untested combinations or outside the approved labeled use. Giles, F. J., et al., Cancer (2001) 92(2):406-413. Like the standard cytarabine-daunorubicin induction therapy, the response rate of patients with relapsed AML to gemtuzumab ozogamicin therapy can be <40%.

Combination therapies with gemtuzumab ozogamicin have been tried with limited success. In one study, gemtuzumab ozogamicin was administered to elderly patients previously untreated for AML by 2-hour IV infusion at a dose of 9 mg/m$^2$ on day 1 and 15, with MICE (mitoxantrone, cytarabine and etoposide) being given for one or two courses within seven days from the response assessment to gemtuzumab ozogamicin (between day 28 and 35 following the last infusion). Significant non-hematologic adverse events included, among others, VOD (6%), arrhythmia (6%), and infection (24%). At the end of the whole induction program, thirteen patients were in complete remission (38.2%) and 3 achieved a complete remission with incomplete platelet recovery (8.8%) for an overall response rate of 47%, not an improvement over existing therapies for AML. Amadori, S., et al., "Sequential Administration of Gemtuzumab Ozogamicin (GO) and Intensive Chemotherapy for Remission Induction in Previously Untreated Patients with AML over the Age of 60: Interim Results of the EORTC Leukemia Group AML-15A Phase II Trial," Blood (2001) 98:587a.

In another study, patients with poor prognosis AML (>70 years age, myelodysplasia, leukemia developing after toxic exposure) were either treated under a protocol designated "AML 9503" in which the patient received two "pulses" of chemotherapy each consisting of 2 gm/m$^2$ of cytarabine (a high dose of cytarabine) administered at time=0 and time=12 hours and mitoxantrone in an amount of 35 mg/m$^2$ immediately after the second cytarabine dose, with the second "pulse" being given 96 hours later, or were treated under a protocol designated "AML 9798" in which the patient received two "pulses" of chemotherapy each consisting of 2 gm/m$^2$ of cytarabine administered at time=0 and time=12 hours and mitoxantrone in an amount of 35 mg/m$^2$ immediately after the second cytarabine dose, with the second "pulse" being given 96 hours later, followed by administration of amifostine. The complete remission rate for AML 9503 was 30% and for AML 9798 was 40%. When the chemotherapy was changed to add a single dose of gemtuzumab ozogamicin in an amount of 9 mg/m$^2$ three days prior to the first pulse of chemotherapy, two of four such treated patients with refractory AML entered complete remission. Preisler, H, D., et al., "Synergistic Antileukemia Effects of Mylotarg and Chemotherapy in AML," Blood (2001) 98:193b.

In a feasibility study, patients <60 years of age received H-DAT 3+10 regimen (daunorubicin 45 mg/m$^2$ days 1, 3, 5; cytarabine 400 mg/m$^2$ bd days 1-10; thioguanine 100 mg/m$^2$ bd days 1-10) with gemtuzumab ozogamicin (3 or 6 mg/m$^2$ given as a 2-hour infusion on day 1). The second course given was H-DAT 3+8 with the same gemtuzumab ozogamicin dose as in course 1. While both the 3 mg/m$^2$ and 6 mg/m$^2$ doses of gemtuzumab ozogamicin were tolerated in these two regimens, increased liver toxicity was seen when gemtuzumab ozogamicin was given at 6 mg/m$^2$ in the first course and it was decided to thereafter use 3 mg/m$^2$ of gemtuzumab ozogamicin in courses 1 and 2. Kell, J. W., et al., "Effects of Mylotarg™ (Gemtuzumab Ozogamicin, GO) in Combination with Standard Induction Chemotherapy in the Treatment of Acute Myeloid Leukaemia (AML): A Feasibility Study," Blood (2001) 98:123a-124a.

In a further study, patients <60 years of age were given H-DAT 3+10 (daunorubicin 50 mg/m$^2$ daily by slow IV push on days 1, 3, 5; cytarabine 200 mg/m$^2$ IV push bd days 1-10; thioguanine 100 mg/m$^2$ bd oral days 1-10) or S-DAT 3+10 (daunorubicin 50 mg/m$^2$ daily by slow IV push on days 1, 3, 5; cytarabine 100 mg/m$^2$ IV push bd days 1-10; thioguanine 100 mg/m$^2$ bd oral days 1-10) with 3 or 6 mg/m$^2$ gemtuzumab ozogamicin as induction therapy. A second course of H-DAT 3+8 (daunorubicin 50 mg/m$^2$ daily by slow IV push on days 1, 3, 5; cytarabine 200 mg/m$^2$ IV push bd days 1-8; thioguanine 100 mg/m$^2$ bd oral days 1-10) or S-DAT 3+8 (daunorubicin 50 mg/m$^2$ daily by slow IV push on days 1, 3, 5; cytarabine 100 mg/m$^2$ IV push bd days 1-8; thioguanine 100 mg/m$^2$ bd oral days 1-10) was given with or without gemtuzumab ozogamicin in an amount of 3 mg/m$^2$. Consolidation therapy consisted of MACE (MACE: Amsacarine 100 mg/m² daily by one hour infusion (in 5% dextrose on days 1-5); cytarabine 200 mg/m² by daily continuous IV infusion days 1-5, Etoposide 100 mg/m² daily by one hour IV infusion days 1-5) chemotherapy with or without gemtuzumab ozogamicin in an amount of 3 mg/m². Patients who received gemtuzumab ozogamicin in courses 1 and 2 had delayed hematological recovery and VOD, one of whom died. The 6 mg/m² dose of gemtuzumab ozogamicin was also associated with increased liver toxicity. It was concluded that 3 mg/m² gemtuzumab ozogamicin can be given with H-DAT 3+10 in course 1 and in course 3 with MACE, but that two courses of gemtuzumab ozogamicin in induction or an increase of the dose of gemtuzumab ozogamicin to 6 mg/m² is associated with increased toxicity and not recommended. Burnett, A. K. and Kell, J., "The Feasibility of Combining Immunoconjugate and Chemotherapy in AML," Hematology J. (June 2002) Vol. 3, supp. 1, p. 156.

In another preliminary study to assess safety and efficacy, gemtuzumab ozogamicin was given to de novo and relapsed/refractory AML patients >60 years old in a combination therapy with cytarabine. Six patients were treated with cytarabine by continuous infusion in an amount of 100 mg/m²/day on days 1 to 7 and gemtuzumab ozogamicin in an amount of 6 mg/m² on days 1 and 15. While the combination was well tolerated, four patients died. To reduce the duration of myelosuppression following induction therapy, gemtuzumab ozogamicin was administered on days 1 and 8 in an amount of 6 mg/m² on day 1 and 4 mg/m² on day 8. Of seven patients who were treated, three achieved complete remission. Durrant, S., et al., Proc. Amer. Soc. Clin. Oncol. (2002) 21:271a.

To assess the safety and efficacy of gemtuzumab ozogamicin as part of combination therapy for AML, a phase I/II study was developed in the United States of America combining gemtuzumab ozogamicin with cytarabine and daunorubicin. The phase I portion of the study began in October 2000 and a preliminary report was published at the 43$^{rd}$ American Society of Hematology Annual Meeting electronically on Nov. 6, 2001 and in print on Nov. 7, 2001. DeAngelo, D., et al., "Preliminary Report of the Safety and Efficacy of Gemtuzumab Ozogamicin (Mylotarg®) Given in Combination with Cytarabine and Daunorubicin in Patients with Acute Myeloid Leukemia", Blood (2001) 98:199(b). That report described the treatment of three patients, one with de novo AML and two with relapsed/refractory AML, with cytarabine in an amount of 100 mg/m²/day by continuous infusion on days 1 to 7, daunorubicin in an amount of 45 mg/m² on days 1 to 3, and gemtuzumab ozogamicin in an amount of 6 mg/m² on day 4 (dosage group 1). The combination was well tolerated, no dose-limiting toxicity (DLT) was observed, and two patients achieved a remission. Three patients with relapsed/refractory AML then were enrolled in the next dosage group in which the dose of gemtuzumab ozogamicin was escalated to 9 mg/m² (dosage group 2), with the combination well tolerated, but all three patients were nonresponders. Six additional patients, three with de novo AML and three with relapsed/refractory AML, were enrolled at the dosage level of 9 mg/m². Therapy was again well tolerated, and no DLT was observed. There were, however, 2 episodes of grade 3 non-drug-related elevations of ALT/AST and 2 episodes of grade 4 non-drug-related dyspnea. All 3 patients with de novo AML achieved remission and recovered both an ANC >1500/⊠L and platelets >100,000/⊠L on days 26, 28, and 36, respectively. Patients then were enrolled in the next dosage group in which the cytarabine dose was increased to 200 mg/m²/day (dosage group 3). Infusion of the combination therapy was well tolerated, but DLT was observed in four of six patients enrolled in this group with one patient with refractory AML developing hepatic VOD soon after completing induction therapy and dying on day 28. Another patient with de novo AML died of cardiac arrest on day 24 and also had reversible grade 3 elevation of ALT. In light of the foregoing results, it was concluded that six additional patients would be enrolled in dosage group 1 to expand the safety data, and if the combination of cytarabine 100 mg/m²/day, daunorubicin 45 mg/m², and gemtuzumab ozogamicin 6 mg/m² would be found to be well tolerated in this expanded group, then the phase II portion of the study would begin and approximately 45 patients with de novo AML would be enrolled. DeAngelo, D., et al., supra. The efficacy of the combination of cytarabine 100 mg/m²/day, daunorubicin 45 mg/m², and gemtuzumab ozogamicin 6 mg/m² could not be determined based on the limited number of patients enrolled in the phase I portion of the study or the efficacy of this combination compared to the efficacy of standard chemotherapy for AML.

Myelodysplastic syndrome (MDS) is a group of syndromes (preleukemia, refractory anemias, Ph-negative chronic myelocytic leukemia, chronic myelomonocytic leukemia, agnogenic myeloid metaplasia) commonly seen in patients >50 years old. Its incidence is unknown, but it is increasing, probably in part due to the increasing proportion of elderly in the population and an increase in treatment-associated leukemias. Exposure to benzene and radiation may be related to its development. In the preleukemic phase of some of the secondary leukemias (e.g., after drug or toxic exposure), altered and defective cellular production may be seen with diagnostic features of myelodysplasia. *The Merck Manual*, Sec. 11, Ch. 138 (17$^{th}$ ed. 1999).

MDS is characterized by clonal proliferation of hematopoietic cells, including erythroid, myeloid, and megakaryocytic forms. The bone marrow is normal or hypercellular, and ineffective hematopoiesis causes variable cytopenias, the most frequent being anemia. The disordered cell production is also associated with morphologic cellular abnormalities in marrow and blood. Extramedullary hematopoiesis may occur, leading to hepatomegaly and splenomegaly. Myelofibrosis is occasionally present at diagnosis or may develop during the course of MDS. The MDS clone is unstable and tends to progress to AML. The prognosis of a patient with MDS is highly dependent on FAB classification and on any associated disease. Patients with refractory anemia or refractory anemia with sideroblasts are less likely to progress to the more aggressive forms and may die of unrelated causes. *The Merck Manual*, Sec. 11, Ch. 138 (17$^{th}$ ed. 1999).

There is no established treatment for MDS. Therapy is supportive with RBC transfusions, platelet transfusions for bleeding, and antibiotic therapy for infection. In some patients, cytokine therapy (erythropoietin to support red blood center needs, granulocyte colony-stimulating factor to manage severe symptomatic granulocytopenia, and, when available, thrombopoietin for severe thrombocytopenia) can serve as important hematopoietic support. Allogeneic bone marrow transplantation is not recommended for patients >50 years old. Colony-stimulating factors (e.g., granulocyte colony-stimulating factor, granulocyte-macrophage colony-stimulating factor) increase neutrophil counts, and erythropoietin increases RBC production in 20 to 25% of cases, but survival advantage has not been shown. Response of MDS to AML chemotherapy is similar to that of AML, after age and karyotype are considered. *The Merck Manual*, Sec. 11, Ch. 138 (17$^{th}$ ed. 1999).

Thus, there is a need for an improved treatment for patients with acute leukemia or myelodysplastic syndrome which will produce a higher rate of complete remission, thereby increasing the survival prospects of such patients. It has been surprisingly been found that a combination therapy employing an anti-CD33 cytotoxic conjugate in combination with an anthracycline and a pyrimidine or purine nucleoside analog, in particular, gemtuzumab ozogamicin, daunorubicin, and cytarabine, respectively, a significant improvement in efficacy compared to the combination therapy of daunorubicin and cytarabine or to gemtuzumab ozogamicin alone.

SUMMARY OF THE INVENTION

The present invention provides a method of treating acute leukemia or MDS comprising administering to a patient in need of said treatment an anti-CD33 cytotoxic conjugate in combination with at least one compound selected from the group consisting of an anthracycline and a pyrimidine or purine nucleoside analog in an amount effective to ameliorate the symptoms of said acute myelogenous leukemia or said myelodysplastic syndrome. The acute leukemia being treated is preferably AML.

In a preferred embodiment, the cytotoxin in the anti-CD33 cytotoxic conjugate is selected from the group consisting of a calicheamicin and an esperamicin.

In another preferred embodiment, the anthracycline is selected from the group consisting of doxorubicin, daunorubicin, idarubicin, aclarubicin, zorubicin, mitoxantrone, epirubicin, carubicin, nogalamycin, menogaril, pitarubicin, and valrubicin.

In another preferred embodiment, the pyrimidine or purine nucleoside analog is selected from the group consisting of cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, and tubercidin.

The present invention further provides a method of treatment of a patient having acute leukemia or MDS, comprising administering to the patient: (a) gemtuzumab ozogamicin in an amount of about 3 mg/m$^2$ to about 9 mg/m$^2$ per day; (b) daunorubicin, preferably daunorubicin hydrochloride, in an amount of about 45 mg/m$^2$ to about 60 mg/m$^2$ per day; and (c) cytarabine in an amount of about 100 mg/m$^2$ to about 200 mg/m$^2$ per day.

In a preferred embodiment, the gemtuzumab ozogamicin is in an amount of about 6 mg/m$^2$ per day.

In another preferred embodiment, the daunorubicin, preferably daunorubicin hydrochloride, is in an amount of 45 mg/m$^2$ per day.

In another preferred embodiment, the cytarabine is in an amount of 100 mg/m$^2$ per day.

The present invention further provides a method of treating acute leukemia or MDS syndrome comprising administering to a patient in need of treatment thereof: (a) gemtuzumab ozogamicin in an amount of about 3 mg/m$^2$ to 9 mg/m$^2$ for one day; (b) daunorubicin in an amount of about 45 mg/m$^2$ to 60 mg/m$^2$ per day for three days; and (c) cytarabine in an amount of about 100 mg/m$^2$ to 200 mg/m$^2$ per day for at least seven days.

In a preferred embodiment, the daunorubicin is administered on the first three days that cytarabine is administered, preferably in an amount of 45 mg/m$^2$ per day.

In another preferred embodiment, the cytarabine is administered for ten days, more preferably for seven days, and preferably in an amount of 100 mg/m$^2$ per day.

In another preferred embodiment, the gemtuzumab ozogamicin is administered to the patient on the fourth day that cytarabine is administered to the patient, preferably in an amount of 6 mg/m$^2$.

In another preferred embodiment, the cytarabine is administered by continuous infusion, the daunorubicin, preferably daunorubicin hydrochloride, is administered by intravenous bolus, and the gemtuzumab ozogamicin is administered by 2-hour infusion.

The present invention further provides a pharmaceutical combination for enhanced induction of remission in a patient having acute leukemia or MDS comprising: (a) an anti-CD33 cytotoxic conjugate, wherein the cytotoxin in the anti-CD33 cytotoxic conjugate is selected from the group consisting of a calicheamicin and an esperamicin; (b) an anthracycline selected from the group consisting of doxorubicin, daunorubicin, idarubicin, aclarubicin, zorubicin, mitoxantrone, epirubicin, carubicin, nogalamycin, menogaril, pitarubicin, and valrubicin; and (c) a pyrimidine or purine nucleoside analog selected from the group consisting of cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, and tubercidin.

The present invention further provides a pharmaceutical combination for enhanced induction of remission in a patient having acute leukemia or MDS comprising gemtuzumab ozogamicin in an amount of about 3 mg/m$^2$ to about 9 mg/m$^2$ per day, preferably 6 mg/m$^2$ per day, daunorubicin, preferably daunorubicin hydrochloride, in an amount of about 45 mg/m$^2$ to about 60 mg/m$^2$ per day, preferably 45 mg/m$^2$ per day, and cytarabine in an amount of about 100 mg/m$^2$ to about 200 mg/m$^2$ per day, preferably 100 mg/m$^2$ per day.

The present invention further provides a method of treating acute leukemia or MDS comprising:

(a) administering a first course of therapy to a patient in need of treatment comprising (i) administering an anti-CD33 cytotoxic conjugate for one day, wherein the cytotoxin in the anti-CD33 cytotoxic conjugate is selected from the group consisting of a calicheamicin and an esperamicin; (ii) administering an anthracycline selected from the group consisting of doxorubicin, daunorubicin, idarubicin, aclarubicin, zorubicin, mitoxantrone, epirubicin, carubicin, nogalamycin, menogaril, pitarubicin, and valrubicin for up to three days; and (iii) administering a pyrimidine or purine nucleoside analog selected from the group consisting of cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, and tubercidin for up to ten days;

(b) administering a second course of therapy to a patient in need of treatment comprising: (i) administering an anti-CD33 cytotoxic conjugate for one day, wherein the cytotoxin in the anti-CD33 cytotoxic conjugate is selected from the group consisting of a calicheamicin and an esperamicin; (ii) administering an anthracycline selected from the group consisting of doxorubicin, daunorubicin, idarubicin, aclarubicin, zorubicin, mitoxantrone, epirubicin, carubicin, nogalamycin, menogaril, pitarubicin, and valrubicin for up to three days; and (iii) administering a pyrimidine or purine nucleoside analog selected from the group consisting of cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, and tubercidin for up to ten days; and (c) administering a third course of therapy to a patient in need of treatment comprising: (i) administering an anthracycline selected from the group consisting of doxorubicin, daunorubicin, idarubicin, aclarubicin, zorubicin, mitoxantrone, epirubicin, carubicin, nogalamycin, menogaril, pitarubicin, and valrubicin for up to three days; and (ii) administering a pyrimidine or purine nucleoside analog selected from the group consisting of cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, and tubercidin for up to ten days.

The present invention further provides a method of treating acute leukemia or MDS comprising:

(a) administering a first course of therapy to a patient in need of treatment comprising (i) gemtuzumab ozogamicin in an amount of about 3 mg/m$^2$ to about 9 mg/m$^2$, preferably 6 mg/m$^2$, per day for one day; (ii) daunorubicin in an amount of about 45 mg/m$^2$ to about 60 mg/m$^2$, preferably 45 mg/m$^2$, per day for up to three days; and (iii) cytarabine in an amount of about 100 mg/m$^2$ to about 200 mg/m$^2$, preferably 100 mg/m$^2$, per day for up to ten days;

(b) administering a second course of therapy to a patient in need of treatment comprising: (i) gemtuzumab ozogamicin in an amount of about 3 mg/m$^2$ to about 9 mg/m$^2$, preferably 6 mg/m$^2$, per day for one day; (ii) daunorubicin in an amount of about 45 mg/m$^2$ to about 60 mg/m$^2$, preferably 45 mg/m$^2$, per day for up to three days; and (iii) cytarabine in an amount of about 100 mg/m$^2$ to about 200 mg/m$^2$, preferably 100 mg/m$^2$, per day for up to ten days; and (c) administering a third course of therapy to a patient in need of treatment comprising: (i) daunorubicin in an amount of about 45 mg/m$^2$ to about 60 mg/m$^2$, preferably 45 mg/m$^2$, per day for up to three days; and (ii) cytarabine in an amount of about 100 mg/m$^2$ to about 200 mg/m$^2$, preferably 100 mg/m$^2$, per day for up to ten days.

DETAILED DESCRIPTION OF THE INVENTION

This invention provides advantageous pharmaceutical combinations and methods of treatment for acute leukemia, such as AML, and for myelodysplastic syndrome (MDS) which employ an anti-CD33 cytotoxic conjugate, an anthracycline, and a pyrimidine or purine nucleoside analog. The method of treatments and pharmaceutical combinations described herein provide a better rate of complete remission and improved quality of life in such patients than the standard 3+7 regimen of daunorubicin and cytarabine. Surprisingly, a preferred embodiment employing gemtuzumab ozogamicin, daunorubicin, and cytarabine provides a higher rate of complete remission than the standard 3+7 regimen of daunorubicin and cytarabine.

The patients to be treated with the methods of treatment and pharmaceutical combinations provided herein are those who have been untreated for acute leukemia such as AML and are being treated de novo, those who are being treated with induction therapy, those who are being treated with consolidation therapy, those who are being treated after one or more relapses, and those who have MDS.

One composition used in the present invention is an anti-CD33 cytotoxic conjugate in which an anti-CD33 antibody is conjugated with a cytotoxic antitumor or antibiotic, such as a calicheamicin isolated from fermentation of a bacterium, *Micromonospora echinospora* ssp. *calichensis*, or an esperamicin. Calicheamicins are described in U.S. Pat. Nos. 4,970,198; 5,037,651; and 5,079,233. Esperamicins are described in U.S. Pat. Nos. 4,675,187; 4,539,203; 4,554,162; and 4,837,206. The antibody portion of the conjugate binds specifically to the CD33 antigen, a sialic acid-dependent adhesion protein found on the surface of leukemic blasts and immature normal cells of myelomonocytic lineage, but not on normal hematopoietic stem cells, and acts as a targeting unit to deliver the cytotoxic agent to these targeted cells. This antibody is linked to the calicheamicin or esperamicin. When N-acetyl-gamma calicheamicin is used, it is preferred to link the antibody by a bifunctional linker. Such conjugates and methods for making them are described in U.S. Pat. Nos. 5,733,001; 5,739,116; 5,767,285; 5,877,296; 5,606,040; 5,712,374; and 5,714,586, which are incorporated by reference herein in their entirety.

A preferred form of the anti-CD33 cytotoxic conjugate for use in the present invention is gemtuzumab ozogamicin, a chemotherapy agent composed of a recombinant humanized IgG4, kappa antibody conjugated with calicheamicin. Gemtuzumab ozogamicin is available commercially as Mylotarg® (Wyeth Pharmaceuticals, Philadelphia, Pa.). The antibody portion of gemtuzumab ozogamicin binds specifically to the CD33 antigen. Gemtuzumab ozogamicin contains amino acid sequences of which approximately 98.3% are of human origin. The constant region and framework regions contain human sequences while the complementarity-determining regions are derived from a murine antibody (p67.6) that binds CD33. This antibody is linked to N-acetyl-gamma calicheamicin via a bifunctional linker. Gemtuzumab ozogamicin has approximately 50% of the antibody loaded with 4-6 moles calicheamicin per mole of antibody. The remaining 50% of the antibody is not linked to the calicheamicin derivative. Gemtuzumab ozogamicin has a molecular weight of 151 to 153 kDa. Gemtuzumab ozogamicin and methods for making it are described in U.S. Pat. Nos. 5,733,001; 5,739,116; 5,767,285; 5,877,296; 5,606,040; 5,712,374; and 5,714,586, which are incorporated by reference herein in their entirety. When given as a single agent therapy for the treatment of AML, the recommended dose of gemtuzumab ozogamicin is 9 mg/m$^2$, administered as a two-hour intravenous infusion. The recommended treatment course with gemtuzumab ozogamicin alone has been a total of two doses with fourteen days between the doses. In the combination therapy of the present invention, gemtuzumab ozogamicin is given in an amount ranging from about 3 mg/m$^2$ to 9 mg/m$^2$ per day.

U.S. Pat. No. 5,773,001, in col. 62, lines 37-46, and Example 112, describes dosage amounts of calicheamicin conjugates, including gemtuzumab ozogamicin, based on calicheamicin equivalents, i.e., 10 µg calicheamicin/m$^2$ protein, as compared to the clinical dose description based on mg/m$^2$ body-surface. When calicheamicin is loaded onto the antibody, there is approximately 27 µg calicheamicin/mg protein. A 9 mg/m$^2$ dose of gemtuzumab ozogamicin is equivalent to 243 µg calicheamicin/m$^2$ protein. A 6 mg/m$^2$ dose of gemtuzumab ozogamicin is equivalent to 162 µg calicheamicin/m$^2$ protein. A 3 mg/m$^2$ dose of gemtuzumab ozogamicin is equivalent to 81 µg calicheamicin/m$^2$ protein.

Another composition used in the present invention is an anthracycline, an anticancer agent consisting of 3 moieties: a pigmented aglycone, an amino sugar, and a lateral chain. Anthracyclines include doxorubicin, daunorubicin, idarubicin, aclarubicin, zorubicin, mitoxantrone, epirubicin, carubicin, nogalamycin, menogaril, pitarubicin, and valrubicin. See *Merck Index* (13$^{th}$ ed. 2001).

A preferred anthracycline for use in the present invention is daunorubicin. Daunorubicin, also known as daunomycin, is an anthracycline cytotoxic antibiotic of the rhodomycin group obtained from *Streptomyces peucetius*, which is used in the treatment of acute leukemia. *Stedman's Medical Dictionary* (27$^{th}$ ed. 2002). Daunorubicin has a 4-ring anthracycline moiety linked by a glycosidic bond to daunosamine, an amino sugar. Daunorubicin may also be isolated from *Streptomyces coeruleorubidus* and has the following chemical name: (8S-cis)-8-acetyl-10-[(3-amino-2,3,6-trideoxy-(alpha)-L-lyxo-hexopyranosyl)oxy]-7,8,9,10-tetrahydro-6,8,11-trihydroxy- 1-methoxy-5,12-naphthacenedione hydrochloride. Daunorubicin is usually given as the hydrochloride, but doses are expressed in terms of the base.

A preferred form of daunorubicin used in the present invention is daunorubicin hydrochloride, the hydrochloride salt of daunorubicin. Daunorubicin hydrochloride is available commercially as Cerubidine® (Bedford Laboratories, Bedford Ohio). It may be described with the chemical name of (1 S,3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride. Its molecular formula is $C_{27}H_{29}NO_{10}\cdot HCl$ with a molecular weight of 563.99. In the treatment of adult acute nonlymphocytic leukemia, such as AML and ALL, daunorubicin hydrochloride, used as a single agent, has produced complete remission rates of 40 to 50%, and in combination with cytarabine, has produced complete remission rates of 53 to 65%. *Physician's Desk Reference* (56$^{th}$ ed. 2002). Typically, daunorubicin is given daily for three days in an amount of 30 to 45 mg/m$^2$ by intravenous infusion for two to three days. In high-dose regimens, daunorubicin is given daily in an amount of 50 mg/m$^2$ for three days.

Daunorubicin is also available commercially in a daunorubicin citrate liposome injection as DaunoXome® (Gilead Sciences, Inc., Foster City, Calif.). DaunoXome® contains an aqueous solution of the citrate salt of daunorubicin encapsulated within lipid vesicles (liposomes) composed of a lipid bilayer of distearoylphosphatidylcholine and cholesterol (2:1 molar ratio), with a mean diameter of about 45 nm. The lipid to drug weight ratio is 18.7:1 (total lipid:daunorubicin base), equivalent to a 10:5:1 molar ratio of distearoylphosphatidylcholine:cholesterol:daunorubicin. Each vial of DaunoXome® contains daunorubicin citrate equivalent to 50 mg of daunorubicin base, encapsulated in liposomes consisting of 704 mg distearoylphosphatidylcholine and 168 mg cholesterol. The liposomes encapsulating daunorubicin are dispersed in an aqueous medium containing 2,125 mg sucrose, 94 mg glycine, and 7 mg calcium chloride dihydrate in a total volume of 25 ml/vial. The pH of the dispersion is between 4.9 and 6.0. DaunoXome® is administered intravenously over a 60 minute period at a dose of 40 mg/m$^2$, with doses repeated every two weeks.

A third composition used in the present invention is a pyrimidine nucleoside analog or a purine nucleoside analog. Representative of such nucleoside analogs are cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, and tubercidin. See *Merck Index* (13$^{th}$ ed. 2001).

A preferred pyrimidine nucleoside analog used in the present invention is cytarabine, which is also known as arabinosylcytosine (aC, araC), arabinocytidine, or arabinofuranosylcytosine. Chemically, cytarabine is 4-amino-1-(beta)-D-arabinofuranosyl-2(1H)-pyrimidinone, also known as cytosine arabinoside ($C_9H_{13}N_3O_5$, molecular weight 243.22). Cytarabine is a cell cycle phase-specific antineoplastic agent, affecting cells only during the S-phase of cell division. It is a compound of arabinose and cytosine that inhibits the biosynthesis of DNA and is used as a chemotherapeutic agent because of its antiviral and tumor-growth-inhibiting properties. Typically, cytarabine is given in an amount of 100-200 mg/m$^2$ daily for five to ten days by constant intravenous infusion, usually for seven days. Cytarabine can be given in an amount of 100 mg/m$^2$ body-surface twice daily by rapid intravenous injection. However, cytarabine can be given in amounts of up to 3 g/m$^2$ daily. In high-dose regimens, cytarabine is given in doses of up to 3 g/m$^2$ by intravenous infusion for every 12 hours for up to six days.

Cytarabine is also available commercially in a cytarabine liposome injection as DEPOCYT® (Chiron Corporation, Emeryville, Calif.). DepoCyt® is a sterile, injectable suspension of the antimetabolite cytarabine, encapsulated into multivesicular lipid-based particles. Each vial contains 50 mg of cytarabine. Cytarabine, the active ingredient, is present at a concentration of 10 mg/ml and is encapsulated in the particles. Inactive ingredients at their respective approximate concentrations are cholesterol, 4.1 mg/ml; triolein, 1.2 mg/ml; dioleoylphosphatidylcholine (DOPC), 5.7 mg/ml; and dipalmitoylphosphatidylglycerol (DPPG), 1.0 mg/ml. The pH of the product falls within the range from 5.5 to 8.5. DepoCyt® is administered intrathecally.

The present invention provides several methods for treating acute leukemia or MDS. In one method, a patient is given an anti-CD33 cytotoxic conjugate in combination with at least one compound selected from the group consisting of an anthracycline and a pyrimidine or purine nucleoside analog in an amount effective to ameliorate the symptoms of the acute leukemia, such as AML, or MDS. Preferably, the cytotoxin in the anti-CD33 cytotoxic conjugate is a calicheamicin or an esperamicin. The anthracycline is preferably selected from the group consisting of doxorubicin, daunorubicin, idarubicin, aclarubicin, zorubicin, mitoxantrone, epirubicin, carubicin, nogalamycin, menogaril, pitarubicin, and valrubicin. The pyrimidine or purine nucleoside analog is preferably selected from the group consisting of cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, and tubercid. Most preferred is that the cytotoxin in the anti-CD33 conjugate is a calicheamicin, the anthracycline is daunorubicin or daunorubicin hydrochloride, and the pyrimidine nucleoside analog is cytarabine.

In another method of treatment, a patient having acute leukemia or MDS is given gemtuzumab ozogamicin in an amount of about 3 mg/m$^2$ to about 9 mg/m$^2$ per day; daunorubicin, preferably daunorubicin hydrochloride, in an amount of about 45 mg/m$^2$ to about 60 mg/m$^2$ per day; and cytarabine in an amount of about 100 mg/m$^2$ to about 200 mg/m$^2$ per day. Preferably, the gemtuzumab ozogamicin is given in an amount of about 6 mg/m$^2$ per day. The daunorubicin, preferably daunorubicin hydrochloride, is preferably given in an amount of 45 mg/m$^2$ per day. The cytarabine is preferably given in an amount of 100 mg/m$^2$ per day.

In another method of treatment, a patient having acute leukemia or MDS is given gemtuzumab ozogamicin in an amount of about 3 mg/m$^2$ to 9 mg/m$^2$ for one day; daunorubicin in an amount of about 45 mg/m$^2$ to 60 mg/m$^2$ per day for three days; and cytarabine in an amount of about 100 mg/m$^2$ to 200 mg/m$^2$ per day for at least seven days. Preferably, the daunorubicin is administered on the first three days that cytarabine is administered, and is preferably given in an amount of 45 mg/m$^2$ per day. The cytarabine is preferably administered for ten days, more preferably for seven days, and is preferably given in an amount of 100 mg/m$^2$ per day. The gemtuzumab ozogamicin is preferably administered to the patient on the fourth day that cytarabine is administered to the patient, and is preferably given in an amount of 6 mg/m$^2$. In a preferred embodiment, the cytarabine is administered by continuous infusion, the daunorubicin, preferably daunorubicin hydrochloride, is administered by intravenous bolus, and the gemtuzumab ozogamicin is administered by 2-hour infusion.

Pharmaceutical combinations for enhanced induction of remission in a patient having acute leukemia or MDS are also provided by the present invention. One such pharmaceutical combination for enhanced induction of remission in a patient having acute leukemia or MDS comprises an anti-CD33 cytotoxic conjugate, an anthracycline, and a pyrimidine or purine nucleoside analog. The cytotoxin in the anti-CD33 cytotoxic conjugate may be selected from the group consisting of a calicheamicin and an esperamicin. The anthracycline may be selected from the group consisting of doxorubicin, daunorubicin, idarubicin, aclarubicin, zorubicin, mitoxantrone, epirubicin, carubicin, nogalamycin, menogaril, pitarubicin, and valrubicin. The pyrimidine or purine nucleoside analog may be selected from the group consisting of cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, and tubercidin.

Another pharmaceutical combination comprises gemtuzumab ozogamicin in an amount of about 3 mg/m² to about 9 mg/m² per day, preferably 6 mg/m² per day, daunorubicin, preferably daunorubicin hydrochloride, in an amount of about 45 mg/m² to about 60 mg/m² per day, preferably 45 mg/m² per day, and cytarabine in an amount of about 100 mg/m² to about 200 mg/m² per day, preferably 100 mg/m² per day.

The nature of acute leukemias and myelodysplastic syndrome calls for the administration of intensive chemotherapy to induce remission in patients having these diseases. In one embodiment of the present invention, a single course of combination therapy comprises administering to the patient a therapeutically effective amount of an anti-CD33 cytotoxic conjugate, together with one or more chemotherapeutic agents, such as anthracycline, and a pyrimidine or purine nucleoside analog. The present invention also provides treatment regimens in which multiple courses of combination therapy, which include an anti-CD33 cytotoxic conjugate and other chemotherapeutic agents, are administered. Such treatment regimens may be administered from at least two to five courses of treatment, depending upon the drugs being administered, the severity of the disease, and the condition of the patient.

In another method of treatment of the present invention, a patient having acute leukemia or MDS is given three courses of therapy. In the first course of therapy, the patient is given an anti-CD33 cytotoxic conjugate for one day; an anthracycline for up to three days; and a pyrimidine or purine nucleoside analog for up to ten days. The cytotoxin in the anti-CD33 cytotoxic conjugate may be selected from the group consisting of a calicheamicin and an esperamicin. The anthracycline may be selected from the group consisting of doxorubicin, daunorubicin, idarubicin, aclarubicin, zorubicin, mitoxantrone, epirubicin, carubicin, nogalamycin, menogaril, pitarubicin, and valrubicin. The pyrimidine or purine nucleoside analog may be selected from the group consisting of cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, and tubercidin. The first course of therapy is repeated as a second course of therapy in which the patient is given an anti-CD33 cytotoxic conjugate for one day, an anthracycline for up to three days, and a pyrimidine or purine nucleoside analog for up to ten days. A third course of therapy may be given to the patient which comprises the administration to the patient of an anthracycline selected from the group consisting of doxorubicin, daunorubicin, idarubicin, aclarubicin, zorubicin, mitoxantrone, epirubicin, carubicin, nogalamycin, menogaril, pitarubicin, and valrubicin for up to three days, and a pyrimidine or purine nucleoside analog selected from the group consisting of cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, and tubercidin for up to ten days.

In another such method of treatment of acute leukemia or MDS, a patient is given a first course of therapy comprising gemtuzumab ozogamicin in an amount of about 3 mg/m² to about 9 mg/m², preferably 6 mg/m², per day for one day; daunorubicin in an amount of about 45 mg/m² to about 60 mg/m², preferably 45 mg/m², per day for up to three days; and cytarabine in an amount of about 100 mg/m² to about 200 mg/m², preferably 100 mg/m², per day for up to ten days. A second course of therapy is given to the patient comprising gemtuzumab ozogamicin in an amount of about 3 mg/m² to about 9 mg/m², preferably 6 mg/m², per day for one day; daunorubicin in an amount of about 45 mg/m² to about 60 mg/m², preferably 45 mg/m², per day for up to three days; and cytarabine in an amount of about 100 mg/m² to about 200 mg/m², preferably 100 mg/m², per day for up to ten days. A third course of therapy may be administered to the patient comprising daunorubicin in an amount of about 45 mg/m² to about 60 mg/m², preferably 45 mg/m², per day for up to three days, and cytarabine in an amount of about 100 mg/m² to about 200 mg/m², preferably 100 mg/m², per day for up to ten days.

The surprising and unexpected result disclosed herein is the ability of the anti-CD33 cytotoxic conjugate, the anthracycline, and the pyrimidine or purine nucleoside analog to act synergistically in the treatment of various symptoms associated with acute leukemia or MDS. Synergistically" is used herein to refer to a situation where the benefit conveyed by the administration of these antineoplastic compositions in combination is greater than the algebraic sum of the effects resulting from the separate administration of the components of the combination. As shown in the Examples below, the combination treatment of an anti-CD33 cytotoxic conjugate, an anthracycline, and an pyrimidine or purine nucleoside analog is synergistic with respect to treating acute leukemia and increasing the efficacy as measured by complete remission. This combined treatment has the advantage of achieving the same result with a lower dose of the anti-CD33 cytotoxic conjugate, thereby reducing any toxic effect from the conjugate, providing an improved quality of life, and increasing the chances for survival of the patient.

As with the use of other chemotherapeutic drugs, the individual patient will be monitored in a manner deemed appropriate by the treating physician. The combination therapy agents described herein may be administered with immunosuppressive agents, potentiators and side-effect relieving agents as deemed necessary by the treating physician.

In therapeutic applications, the dosages of the agents used in accordance with the invention may vary depending on the agent, the age, weight, and clinical condition of the recipient patient, and the experience and judgment of the clinician or practitioner administering the therapy, among other factors affecting the selected dosage. Generally, the dose should be sufficient to result in complete remission as previously defined. An effective amount of a pharmaceutical agent is that which provides an objectively identifiable improvement as noted by the clinician or other qualified observer. It is especially advantageous to formulate compositions of these antineoplastic compounds in dosage unit form for ease of administration and uniformity of dosage. "Dosage unit form" as used herein refers to physically discrete units suited as unitary dosages for the patients to be treated, each unit containing a predetermined quantity of anti-neoplastic compounds calculated to produce the desired therapeutic effect in association with the required pharmaceutical carrier. As used herein, "pharmaceutically acceptable carrier" includes any and all solvents, dispersion media, coating, antibacterial and antifungal agents, isotonic and absorption delaying agents and the like which are compatible with the active ingredient and with the mode of administration and other ingredients of the formulation and not deleterious to the recipient.

The pharmaceutical compositions of this invention which are found in the combination may also include, depending on the formulation desired, pharmaceutically-acceptable, nontoxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants, or nontoxic, nontherapeutic, nonimmunogenic stabilizers and the like. Effective amounts of such diluent or carrier will be those amounts which are effective to obtain a pharmaceutically acceptable formulation in terms of solubility of components, or biological activity, and the like.

For parenteral therapeutic administration, each antineoplastic compound may be incorporated with a sterile injectable solution. The sterile injectable solution may be prepared by incorporating the antineoplastic compound in the required amount in an appropriate pharmaceutically acceptable carrier, with various other ingredients, followed by filtered sterilization. In the case of dispersions, each may be prepared by incorporating the additional antineoplastic compound into a sterile vehicle which contains the basic dispersion medium and the required other ingredients from those enumerated herein. In the case of sterile injectable solutions, each may be prepared by incorporating a powder of the additional antineoplastic compound and, optionally, any additional desired ingredient from a previously sterile-filtered solution thereof, wherein the powder is prepared by any suitable technique (e.g., vacuum drying and freeze drying). The use of such media and agents is well known in the art (see for example, *Remington's Pharmaceutical Sciences*, 18th Ed. (1990), Mack Publishing Co., Easton, Pa. 18042, pages 1435-1712, the disclosure of which is hereby incorporated by reference). Supplementary active ingredients can also be incorporated into the compositions. The specific dose of the antineoplastic compound is calculated according to the approximate body weight or surface area of the patient. Other factors in determining the appropriate dosage can include the stage of the acute myelogenous leukemia or myelodysplastic syndrome (de novo or relapse), the severity of the disease, the route of administration and the age, sex and medical condition of the patient. Further refinement of the calculations necessary to determine the appropriate dosage for treatment involving each of the herein-mentioned formulations is routinely made by those skilled in the art. Dosages can also be determined through the use of known assays for determining dosages used in conjunction with appropriate dose-response data. Thus, for example, it is within the scope of the invention that doses of the antineoplastic compounds used in the present invention for treating acute myelogenous leukemia or myelodysplastic syndrome can be varied to achieve a desired therapeutic effect.

If oral therapeutic administration is an option, the antineoplastic compound may be incorporated with excipients and used in the form of ingestible tablets, buccal tablets, troches, capsules, elixers, suspensions, syrups, wafers and the like, or it may be incorporated directly with the food in the diet. The tablets, troches, pills, capsules and the like may also contain the following: a binder such as gum tragacanth, acacia, corn starch or gelatin; excipients such as dicalcium phosphate; a disintegrating agent such as corn starch, alginic acid and the like; a lubricant such as magnesium stearate; a sweetening agent such as sucrose, lactose or saccharin; or a flavoring agent such as peppermint, oil of wintergreen or cherry or orange flavoring. When the dosage unit form is a capsule, it may contain, in addition to material of the type described herein, a liquid carrier. Various other materials may be present as a coating or to otherwise modify the physical form of the dosage unit. For instance, tablets, pills or capsules may be coated with shellac, sugar or both. Of course, any material used in preparing any dosage unit form should be pharmaceutically pure and substantially non-toxic in the amounts employed. In addition, the antineoplastic compound may be incorporated into a sustained-release preparation and formulation. The amount of the antineoplastic compound in such therapeutically useful composition is such that a suitable dosage will be obtained.

It is understood that the foregoing detailed description and the following examples are illustrative only and are not to be taken as limitations upon the scope of the invention. Various changes and modifications to the disclosed embodiments, which will be apparent to those skilled in the art, may be made without departing from the spirit and scope of the present invention. Further, all patents, patent applications, and publications cited herein are incorporated herein by reference.

EXAMPLES

Example 1

To assess the safety and efficacy of gemtuzumab ozogamicin as part of a combination therapy for AML, a phase ½ study was developed in the United States of America to combine gemtuzumab ozogamicin with cytarabine and daunorubicin. Patients with relapsed, refractory, or de novo AML were enrolled in phase 1 from October 2000 through November 2001. The maximum tolerated dose was determined to be cytarabine 100 mg/m$^2$/day by continuous infusion on days 1 through 7, daunorubicin 45 mg/m$^2$ by intravenous bolus on days 1 through 3, and gemtuzumab ozogamicin 6 mg/m$^2$ by 2-hour infusion on day 4. The phase 2 portion of the study was open to enrollment on November 2001 and 42 of the planned 45 patients have been enrolled to date.

A detailed safety and efficacy evaluation was performed on the first 19 patients treated with this combination induction regimen and subsequently followed for at least 28 days. There were sixteen men and three women enrolled with a median age of 46 years (range, 20 to 60). One, ten, and three patients were categorized in favorable-, intermediate- and poor-risk cytogenetic groups, respectively. Cytogenetic analysis was not available for five patients. Seventeen patients had baseline bone marrow leukemic blast cell determinations with a median blast percentage of 60% Combination therapy was well tolerated and all nineteen patients completed the planned induction therapy.

Three patients (16%) reported NCI grade 3 fever/chills on the day of gemtuzumab ozogamicin infusion. The incidence of grade 3 AST/ALT elevation was 16%; no grade 3 or 4 hyperbilirubinemia was reported. There were no cases of hepatic veno-occlusive disease/sinusoidal obstruction syndrome. The incidence of grade 3 or 4 infections was 32%. The early treatment mortality rate was 0%. Four patients required re-induction for residual AML with cytarabine and daunorubicin on approximately day 15. One of these patients was taken off study and given re-induction with a high-dose cytarabine (HDAC)-containing regimen on study day 15 and was not evaluable for efficacy.

Fifteen of 18 patients (83%) achieved a complete remission (CR) characterized by the absence of AML blasts from the peripheral blood, no extramedullary AML, ≦5% marrow blasts in a marrow with >20% cellularity, and recovery of peripheral counts to absolute neutrophil count (ANC)≧1500/μL and platelets to ≧100,000/μL. No patients were reported to have complete remission with incomplete platelet recovery (CRp). Of the three non-remission patients, 2 had progressive disease and 1 achieved a marrow remission but required radiation therapy for a residual chloroma. Among CR patients, the median time to recover ANC to ≧1500/μL was 38 days and platelets to ≧100,000/μL was 30 days. Patients have been followed for too short a time to determine duration of remission (median follow-up 193 days).

The combination of cytarabine 100 mg/m²/day, daunorubicin 45 mg/m², and gemtuzumab ozogamicin 6 mg/m² was well tolerated with low hepatotoxicity and resulted in an increase in the CR rate to 83%. Historical control data from the Southwest Oncology Group (SWOG) shows a 60% CR rate with standard therapy of 100 mg/m²/day of cytarabine for seven days and 45 mg/m² of daunorubicin for three days. The combination of cytarabine 100 mg/m²/day, daunorubicin 45 mg/m², and gemtuzumab ozogamicin 6 mg/m² resulted in a markedly improved rate of CR compared to standard therapy.

Example 2

The feasibility of combining gemtuzumab ozogamicin with intensive chemotherapy for induction and/or consolidation was evaluated in 67 patients in a safety study in the United Kingdom prior to the start of the Medical Research Center AML15 trial. The aim was to combine gemtuzumab ozogamicin with chemotherapy planned in the trial, (DAT; Daunorubicin, AraC, Thioguanine, or DA; Daunorubicin AraC; or FLAG-IDA; Fludarabine, AraC, G-CSF, Idarubicin) as course 1. Course 1 was given using gemtuzumab ozogamicin in an amount of 3 mg/m² on day 1 of chemotherapy in 55 patients. Thirty-three patients received gemtuzumab ozogamicin with DAT. Eight patients received gemtuzumab ozogamicin with DA. Fourteen patients received gemtuzumab ozogamicin with FLAG-Ida. Of the 55 patients treated, 41 (85%) entered complete remission with course 1 broken down as follows: (19) DAT=26/32; (2) DA=7/8; and (3) FLAG-Ida=8/8. Prior experience in a separate trial designated MRC AML12 where 720 patients were treated with H-DAT alone in course 1, 64% of those patients achieved complete remission. In the present study, the median time to ANC recovery (1×10⁹/l) was 27 days (range 9-54) and platelets >100×10⁹/l was 30 (range 21-48) which is within the mean+1SD of the 720 patients treated with H-DAT alone in the MRC AML12 trial. Non-hemopoietic toxicity was confined to the liver. Overall the maximum toxicity was Grade 1=5 patients, Grade 2=22 patients, Grade 3=13 patients and Grade 4=10 patients. Of the Grade 3 and 4 toxicities, 7 were felt to be definitely associated with gemtuzumab ozogamicin therapy. A possible contributory factor was the inclusion of Thioguanine. Of the 39 recipients where Thioguanine was included in the schedules, 22 developed Grade 3 or 4 liver toxicity compared with 1 for 16 recipients of non-Thioguanine schedules.

Nine additional patients received H-DAT with 6 mg/m² gemtuzumab ozogamicin and 8 patients achieved complete remission with course 1. Hematological recovery was not prolonged, but 3 patients developed Grade 3 or 4 liver toxicity of whom 2 developed a VOD-like syndrome from which both recovered. A 6 mg/m² dose of gemtuzumab ozogamicin was not considered feasible.

Fifteen patients received gemtuzumab ozogamicin in a dose of 3 mg/m² with courses 1 and 2 (DAT 3+10 and DAT 3+8). ANC recovery was delayed in 5 patients and platelet recovery in 11, and both in 5 patients. Grade 3 or 4 liver toxicity was seen in 3 cases of whom 2 developed a VOD-like syndrome.

Seventeen patients received gemtuzumab ozogamicin in a dose of 3 mg/m² with chemotherapy in course 3 with MACE (MACE: Amsacarine, AraC, Etoposide, or high dose AraC). Only one patient developed greater than Grade 2 liver toxicity. Twelve patients received induction in course 1 with gemtuzumab ozogamicin in a dose of 3 mg/m² and course 3 with gemtuzumab ozogamicin in a dose of 3 mg/m². This appears to be feasible but further study of this regimen is ongoing.

The overall survival of all patients receiving gemtuzumab ozogamicin in a dose of 3 mg/m² with course 1 at 6 months is 73% and at 12 months is 68%. For the patient receiving non-Thioguanine induction with 3 mg/m² of gemtuzumab ozogamicin, the 6 month survival is 91%.

What is claimed is:

1. A method of treating acute leukemia or myelodysplastic syndrome consisting essentially of administering to a patient in need of treatment thereof: (a) gemtuzumab ozogamicin in an amount of about 3 mg/m² to about 9 mg/m² per day; (b) daunorubicin in an amount of about 45 mg/m² to about 60 mg/m² per day; and (c) cytarabine in an amount of about 100 mg/m² to about 200 mg/m² per day.

2. The method according to claim 1, wherein the amount of gemtuzumab ozogamicin is 6 mg/m² per day.

3. The method according to claim 1, wherein the daunorubicin is daunorubicin hydrochloride.

4. The method according to claim 1 or 3, wherein the amount of daunorubicin is 45 mg/m² per day.

5. The method according to claim 1, wherein the amount of cytarabine is 100 mg/m² per day.

6. A method of treating acute leukemia or myelodysplastic syndrome consisting essentially of administering to a patient in need of treatment thereof: (a) gemtuzumab ozogamicin in an amount of about 3 mg/m² to 9 mg/m² for one day; (b) daunorubicin in an amount of about 45 mg/m² to 60 mg/m² per day for three days; and (c) cytarabine in an amount of about 100 mg/m² to 200 mg/m² per day for at least seven days.

7. The method according to claim 6, wherein the daunorubicin is administered to the patient on the first three days that cytarabine is administered to the patient.

8. The method according to claim 6 or 7, wherein the gemtuzumab ozogamicin is administered to the patient on the fourth day that cytarabine is administered to the patient.

9. The method according to claim 6, wherein the cytarabine is administered for ten days.

10. The method according to claim 8, wherein the cytarabine is administered by continuous infusion, the daunorubicin is administered by intravenous bolus, and the gemtuzumab ozogamicin is administered by 2-hour infusion.

11. The method according to claim 8, wherein the cytarabine is administered in an amount of 100 mg/m²/day, the daunorubicin is administered in an amount of 45 mg/m², and the gemtuzumab ozogamicin is administered in an amount of 6 mg/m².

12. The method according to claim 6, wherein the daunorubicin is daunorubicin hydrochloride.

13. A pharmaceutical combination for enhanced induction of remission in a patient having acute leukemia or myelodysplastic syndrome consisting essentially of gemtuzumab ozogamicin in an amount of about 3 mg/m$^2$ to about 9 mg/m$^2$, daunorubicin in an amount of about 45 mg/m$^2$ to about 60 mg/m$^2$, and cytarabine in an amount of about 100 mg/m$^2$ to about 200 mg/m$^2$.

14. The pharmaceutical combination of claim 13, wherein the daunorubicin is daunorubicin hydrochloride.

15. The pharmaceutical combination of claim 13 wherein the gemtuzumab ozogamicin is in an amount of about 6 mg/m$^2$.

16. The pharmaceutical combination of claim 13 or 14, wherein the daunorubicin is in an amount of about 45 mg/m$^2$.

17. The pharmaceutical combination of claim 13, wherein the cytarabine is in an amount of 100 mg/m$^2$.

18. A pharmaceutical combination for enhanced induction of remission in a patient having acute leukemia or myelodysplastic syndrome consisting essentially of gemtuzumab ozogamicin in an amount of 6 mg/m$^2$, daunorubicin in an amount of 45 mg/m$^2$, and cytarabine in an amount of 100 mg/m$^2$.

19. A method of treating acute myelogenous leukemia or myelodysplastic syndrome consisting essentially of: (a) administering a first course of therapy to a patient in need of treatment consisting essentially of: (i) gemtuzumab ozogamicin in an amount of about 3 mg/m$^2$ to about 9 mg/m$^2$ per day for one day; (ii) daunorubicin in an amount of about 45 mg/m$^2$ to about 60 mg/m$^2$ per day for up to three days; and (iii) cytarabine in an amount of about 100 mg/m$^2$ to about 200 mg/m$^2$ per day for up to ten days; (b) administering a second course of therapy to a patient in need of treatment consisting essentially of: (i) gemtuzumab ozogamicin in an amount of about 3 mg/m$^2$ to about 9 mg/m$^2$ per day for one day; (ii) daunorubicin in an amount of about 45 mg/m$^2$ to about 60 mg/m$^2$ per day for up to three days; and (iii) cytarabine in an amount of about 100 mg/m$^2$ to about 200 mg/m$^2$ per day for up to ten days; and (c) administering a third course of therapy to a patient in need of treatment consisting essentially of: (i) daunorubicin in an amount of about 45 mg/m$^2$ to about 60 mg/m$^2$ per day for up to three days; and (ii) cytarabine in an amount of about 100 mg/m$^2$ to about 200 mg/m$^2$ per day for up to ten days.

20. A method of treating acute myelogenous leukemia or myelodysplastic syndrome consisting essentially of: (a) administering a first course of therapy to a patient in need of treatment consisting essentially of: (i) gemtuzumab ozogamicin in an amount of 6 mg/m$^2$ per day for one day; (ii) daunorubicin in an amount of 45 mg/m$^2$ per day for up to three days; and (iii) cytarabine in an amount of 100 mg/m$^2$ to about 200 mg/m$^2$ per day for up to ten days; (b) administering a second course of therapy to a patient in need of treatment consisting essentially of: (i) gemtuzumab ozogamicin in an amount of 6 mg/m$^2$ per day for one day; (ii) daunorubicin in an amount of 45 mg/m$^2$ to per day for up to three days; and (iii) cytarabine in an amount of 100 mg/m$^2$ per day for up to ten days; and (c) administering a third course of therapy to a patient in need of treatment consisting essentially of: (i) daunorubicin in an amount of 45 mg/m$^2$ per day for up to three days; and (ii) cytarabine in an amount of 100 mg/m$^2$ per day for up to ten days.

\* \* \* \* \*